(12) United States Patent
Chang et al.

(10) Patent No.: US 10,987,064 B2
(45) Date of Patent: Apr. 27, 2021

(54) LUNG SOUND MONITORING DEVICE AND LUNG SOUND MONITORING METHOD THEREOF

(71) Applicant: Industrial Technology Research Institute, Hsinchu (TW)

(72) Inventors: Cheng-Li Chang, Hsinchu (TW); Yi-Fei Luo, Zhudong Township (TW); Ho-Hsin Lee, Hsinchu (TW); Chun-Fu Yeh, Xingang Township (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 338 days.

(21) Appl. No.: 16/120,985

(22) Filed: Sep. 4, 2018

(65) Prior Publication Data

US 2019/0239819 A1 Aug. 8, 2019

Related U.S. Application Data

(60) Provisional application No. 62/626,928, filed on Feb. 6, 2018.

(30) Foreign Application Priority Data

Mar. 21, 2018 (TW) .................................. 107109623

(51) Int. Cl.
| | |
|---|---|
| *A61B 5/00* | (2006.01) |
| *A61B 7/00* | (2006.01) |
| *A61B 5/08* | (2006.01) |
| *G10L 25/66* | (2013.01) |
| *G10L 25/18* | (2013.01) |

(52) U.S. Cl.
CPC .............. *A61B 5/7257* (2013.01); *A61B 5/08* (2013.01); *A61B 5/6823* (2013.01);
(Continued)

(58) Field of Classification Search
CPC ......... A61B 5/7257; A61B 7/003; A61B 5/08; A61B 5/7225; A61B 5/74; A61B 5/6823;
(Continued)

(56) References Cited

U.S. PATENT DOCUMENTS

| | | | |
|---|---|---|---|
| 5,928,156 | A | 7/1999 | Krumbiegel et al. |
| 7,981,045 | B2 | 7/2011 | Suzuki et al. |

(Continued)

FOREIGN PATENT DOCUMENTS

| | | |
|---|---|---|
| CN | 106021948 A | 10/2016 |
| TW | 558434 | 10/2003 |

(Continued)

OTHER PUBLICATIONS

Taiwanese Office Action and Search Report, dated Oct. 29, 2018, for Taiwanese Application No. 107109823.

*Primary Examiner* — Jacqueline Cheng
*Assistant Examiner* — Tho Q Tran
(74) *Attorney, Agent, or Firm* — Birch, Stewart, Kolasch & Birch, LLP

(57) ABSTRACT

A lung sound monitoring device is provided. The lung sound monitoring device includes an acoustic sensor and a processor. The acoustic sensor is configured to capture the chest cavity sound of a subject at a first monitoring position on the subject and convert the chest cavity sound into a first chest cavity sound signal. The processor is configured to receive the first chest cavity sound signal and perform a filter process to obtain a first lung sound signal, and convert the first lung sound signal into a first lung sound spectrum using time-domain frequency-domain conversion. The processor acquires a first intensity index according to the first lung sound spectrum, and outputs a prompt signal according to the first intensity index to indicate whether the first monitoring position is a qualified monitoring position.

18 Claims, 8 Drawing Sheets

(52) U.S. Cl.
CPC .............. *A61B 5/7225* (2013.01); *A61B 5/74* (2013.01); *A61B 7/003* (2013.01); *G10L 25/18* (2013.01); *G10L 25/66* (2013.01); *A61B 2562/0204* (2013.01)

(58) Field of Classification Search
CPC ... A61B 2562/0204; A61B 7/04; G10L 25/66; G10L 25/18; G10L 25/48
USPC ........................................................ 600/529
See application file for complete search history.

(56) References Cited

U.S. PATENT DOCUMENTS

| | | |
|---|---|---|
| 8,506,480 B2 | 8/2013 | Banet et al. |
| 2005/0033144 A1 | 2/2005 | Wada |
| 2005/0119586 A1 | 6/2005 | Coyle et al. |
| 2011/0125044 A1 | 5/2011 | Rhee et al. |
| 2011/0222697 A1* | 9/2011 | Dong .................... A61B 7/026 381/67 |
| 2015/0094914 A1 | 4/2015 | Abreu |
| 2016/0100817 A1* | 4/2016 | Hussain .................. A61B 7/04 600/301 |
| 2016/0361041 A1 | 12/2016 | Barsimantov et al. |
| 2017/0071506 A1 | 3/2017 | Dwarika |
| 2017/0135649 A1 | 5/2017 | Kametani et al. |
| 2017/0325779 A1 | 11/2017 | Spina et al. |
| 2018/0021010 A1 | 1/2018 | Stamatopoulos et al. |

FOREIGN PATENT DOCUMENTS

| | | |
|---|---|---|
| TW | 200706160 | 2/2007 |
| TW | 200838474 | 10/2008 |

\* cited by examiner

LUNG SOUND MONITORING DEVICE AND LUNG SOUND MONITORING METHOD THEREOF

CROSS REFERENCE TO RELATED APPLICATIONS

This Application claims priority of Taiwan Patent Application No. 107109623, filed on Mar. 21, 2018, the entirety of which is incorporated by reference herein. Furthermore, this application claims the benefit of U.S. Provisional Application No. 62/626,928 filed on Feb. 6, 2018, the entirety of which is incorporated by reference herein.

BACKGROUND

Field of the Disclosure

The present disclosure relates to a lung sound monitoring device, and relates to a lung sound monitoring device and a lung sound monitoring method that can assist in determining the suitable position of capturing lung sound.

Description of the Related Art

At present, the diagnosis of pulmonary obstruction in patients is accomplished through auscultation by an experienced clinician. The clinician must personally hold a stethoscope and make a diagnosis that draws upon his personal experience after carefully auscultating several specific sites on the patient's chest. Therefore, breathing sounds are an important basis for judging the physiological condition of the lungs.

However, patients with symptoms such as Chronic Obstructive Pulmonary Disease (COPD) often have weaker breath sounds due to pulmonary obstruction. When recording a lung sound, the stethoscope must be accurately placed between the ribs in a specific position, and it is not easy to obtain a good capturing position in operation. Moreover, continuous monitoring of lung sounds for follow-up condition tracking and analysis is very much needed by respiratory intensive care units, but there is currently no physiological monitor capable of continuously recording lung sounds.

SUMMARY

A detailed description is given in the following embodiments with reference to the accompanying drawings.

The present disclosure provides a lung sound monitoring device, comprising an acoustic sensor and a processor. The acoustic sensor is configured to capture the chest cavity sound of a subject at a first monitoring position on the subject and convert the chest cavity sound into a first chest cavity sound signal. The processor is configured to receive the first chest cavity sound signal and perform a filter process to obtain a first lung sound signal, and convert the first lung sound signal into a first lung sound spectrum using time-domain frequency-domain conversion. The processor acquires a first intensity index according to the first lung sound spectrum, and outputs a prompt signal according to the first intensity index to indicate whether the first monitoring position is a qualified monitoring position.

The present disclosure further provides a lung sound monitoring device, wherein the processor generates the prompt signal according to whether the first intensity index exceeds a threshold; when the first intensity index does not exceed the threshold, the prompt signal is a movement instruction signal to indicate that the lung sound monitoring device needs to be moved to a second monitoring position on the subject; when the first intensity index exceeds the threshold, the prompt signal is a positioning-completion signal, and the lung sound monitoring device starts to record the lung sound of the subject. After outputting the movement instruction signal and the lung sound monitoring device moving to the second monitoring position on the subject, the acoustic sensor captures the chest cavity sound of the subject at the second monitoring position and converts the chest cavity sound into a second chest cavity sound signal. The processor receives the second chest cavity sound signal and performs the filter process to obtain a second lung sound signal, and converts the second lung sound signal into a second lung sound spectrum using time-domain frequency-domain conversion; the processor acquiring a second intensity index according to the second lung sound spectrum. The processor further compares the first intensity index and the second intensity index to determine whether the first monitoring position or the second monitoring position is a suitable lung sound monitoring position.

The present disclosure also provides a lung sound monitoring method for a lung sound monitoring device which comprises an acoustic sensor and a processor, the method comprising capturing the chest cavity sound of a subject at a first monitoring position on the subject by the acoustic sensor and converting the chest cavity sound into a first chest cavity sound signal; receiving the first chest cavity sound signal by the processor and performing a filter process to obtain a first lung sound signal, and converting the first lung sound signal into a first lung sound spectrum using time-domain frequency-domain conversion; acquiring a first intensity index according to the first lung sound spectrum by the processor, and outputting a prompt signal according to the first intensity index to indicate whether the first monitoring position is a qualified monitoring position.

BRIEF DESCRIPTION OF THE DRAWINGS

The present disclosure can be more fully understood by reading the subsequent detailed description and examples with references made to the accompanying drawings, wherein.

DETAILED DESCRIPTION OF THE DISCLOSURE

The following description is of the best-contemplated mode of carrying out the disclosure. This description is made for the purpose of illustrating the general principles of the disclosure and should not be taken in a limiting sense. The scope of the disclosure is best determined by reference to the appended claims.

Figure 1:
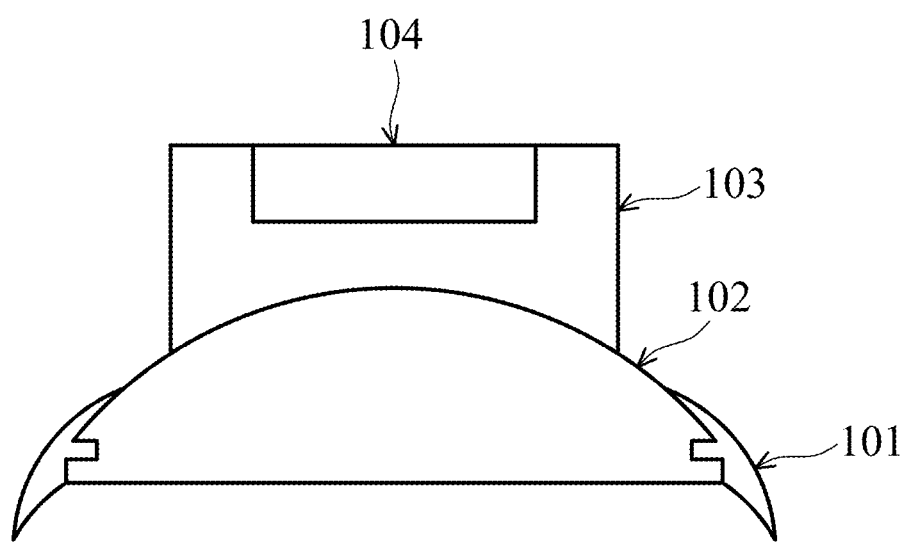
FIG. 1 is a schematic diagram of a lung sound monitoring device according to an embodiment of the present disclosure.

FIG. 1 is a schematic diagram of a lung sound monitoring device 100 according to an embodiment of the present disclosure. FIG. 1 is a schematic cross-sectional view of a lung sound monitoring device 100. The lung sound monitoring device 100 includes an attachment suction cup 101, a sound collection chamber 102, a main circuit portion 103, and a prompt output device 104. The attachment suction cup 101 may be a soft material sucker or adhesive for attaching to the subject's body and adapting to different body shapes. The lung sound monitoring device 100 is attached to the thoracic cavity (chest cavity) of the subject's chest or back using the attachment suction cup 101. The sound collection chamber 102 may be a cavity formed of a light and rigid material, such as a titanium alloy single material or a composite material coated with a metal film on the surface of the plastic material. The attachment suction cup 101 is attached to the subject, and a sealed cavity is formed with the attaching surface of the subject. The sound collection chamber 102 cooperates with the main circuit portion 103 to capture the chest cavity sound of the subject. The main circuit portion 103 may include a microphone, a processor, and other circuits for collecting the chest cavity sound of the subject and performing subsequent data analysis. The main circuit portion 103 further includes a prompt output device 104. The prompt output device 104 may output a signal such as a sound, a light signal, or a vibration to alert the subject or the medical care assistant so that they can determine whether the position of the lung sound monitoring device 100 is a good one with which to capture the chest cavity sound.

Figure 2:
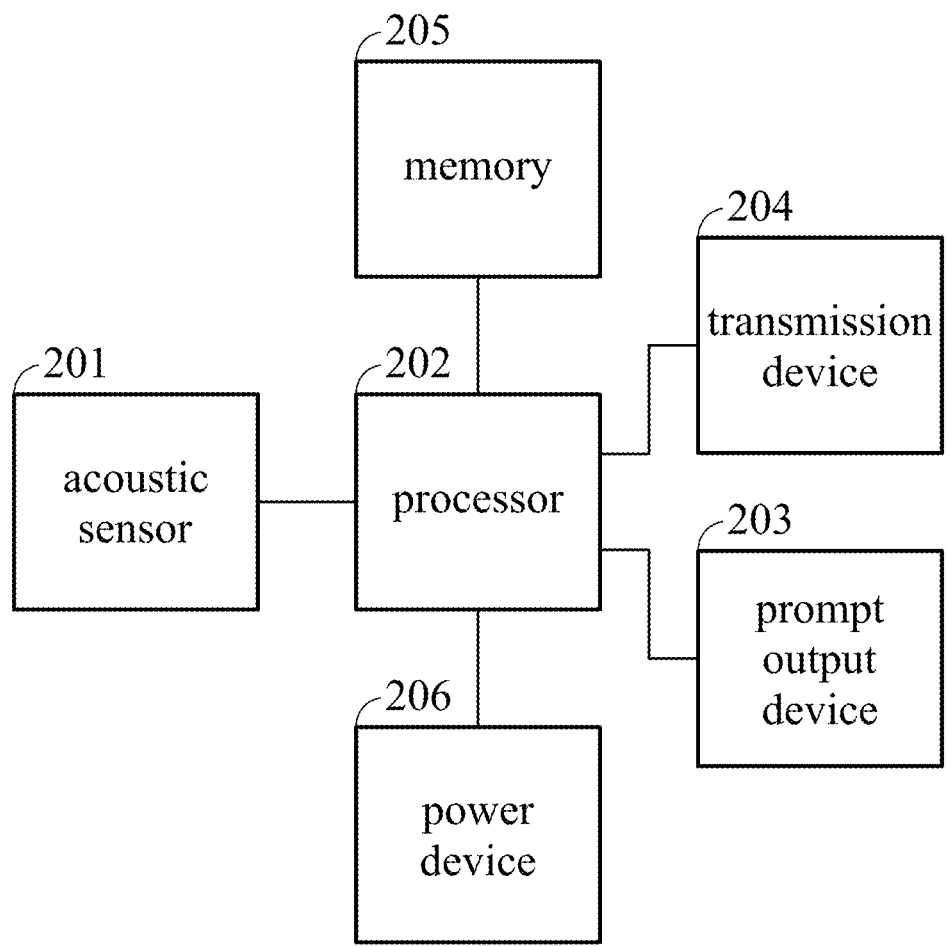
FIG. 2 is a block diagram of the main circuit portion of the lung sound monitoring device shown in FIG. 1.

FIG. 2 is a block diagram of the main circuit portion of the lung sound monitoring device 100 shown in FIG. 1. As shown in FIG. 2, the main circuit portion 200 includes an acoustic sensor 201, a processor 202, a prompt output device 203, a transmission device 204, a memory 205, and a power device 206. The acoustic sensor 201 may be an omnidirectional, unidirectional, or bi-directional microphone, and the present disclosure is not limited thereto. In this embodiment, the acoustic sensor 201 captures the chest cavity sound of the subject at a first monitoring position on the subject and converts the chest cavity sound into a first chest cavity sound signal. The processor 202 may be a central processing unit (CPU), a microcontroller (MCU), an application-specific integrated circuit (ASIC), or the like, and the present disclosure is not limited thereto. The processor 202 is electrically connected to the acoustic sensor 201, receives the first chest cavity sound signal, and performs the preceding signal processing to obtain the first lung sound signal of the lung sound of the subject. Then, the processor 202 converts the time domain of the lung sound signal of the subject into the frequency domain to obtain the first lung sound spectrum. The processor 202 calculates the first intensity index, and outputs a prompt signal according to the first intensity index to indicate whether the first monitoring position is a qualified monitoring position. The chest sound signal captured from the above-mentioned qualified monitoring position where the lung sound monitoring device located is clinically sufficient to represent the lung sound of the subject, and can be used to assist the professional medical care assistant to diagnose or analyze the disease condition of the subject. The detailed process flow of the processor 202 will be described later within FIGS. 3A-3D.

The prompt output device 203 may include a speaker, a light bulb, an LED lamp, a vibrator, or a combination thereof. The prompt output device 203 is configured to receive the prompt signal sent by the processor 202, wherein the prompt signal is generated by the prompt output device 203 in the form of vibration, sound, light signal, or a combination thereof. The prompt output device 203 outputs a prompt signal to let the subject or medical care assistant know whether the current monitoring position of the lung sound monitoring device 100 is a qualified (good) monitoring position. For example, the prompt output device 203 can output a voice through the speaker that can instruct the subject or medical care assistant to move the lung sound monitoring device 100 to the second monitoring position to capture another chest cavity sound. Or indicate that the first monitoring position is a qualified (good) monitoring position, and the lung sound monitoring device 100 can continuously record the chest cavity sound using the acoustic sensor 201. In another embodiment, the prompt output device 203 can also display the intensity of the first intensity index calculated by the processor 202 in a long strip through a plurality of light bulbs, or the prompt output device 203 can display different colors such as red, blue and green through a light bulb to distinguish whether the monitoring position is a qualified monitoring position. Similarly, the prompt output device 203 can also indicate the strength of the first intensity index through the vibration intensity output by the vibrator, and the present disclosure is not limited thereto.

In the present embodiment, the main circuit portion 200 further includes a transmission device 204. The transmission device 204 transmits data such as the first chest cavity sound signal, the first lung sound signal or the first intensity index to a storage device or a cloud server (not shown) through a wireless or wired transmission for subsequent records, monitoring or analysis. In addition, the transmission device 204 can also transmit the lung sound data continuously recorded by the acoustic sensor 201 to the above server or connect with the respiratory intensive care unit to monitor and analyze the respiratory physiological information of the subject in real time.

The main circuit portion 200 further includes a memory 205 and a power device 206. The memory 205 is used to store the threshold of the intensity index and the information of the lung sound signal, the lung sound spectrum and the intensity index calculated by the processor 202 and the like. Therefore, the processor 202 is enabled to compare data of different time sequences and output a prompt signal. The power device 206 is used to supply the power required by the lung sound monitoring device 100 to make it portable and wearable. In addition, the lung sound monitoring device 100 may further include fasteners such as bandages and straps (not shown) to allow the subject to fix the lung sound monitoring device 100 in the chest position of the subject, making it wearable.

Figure 3A:
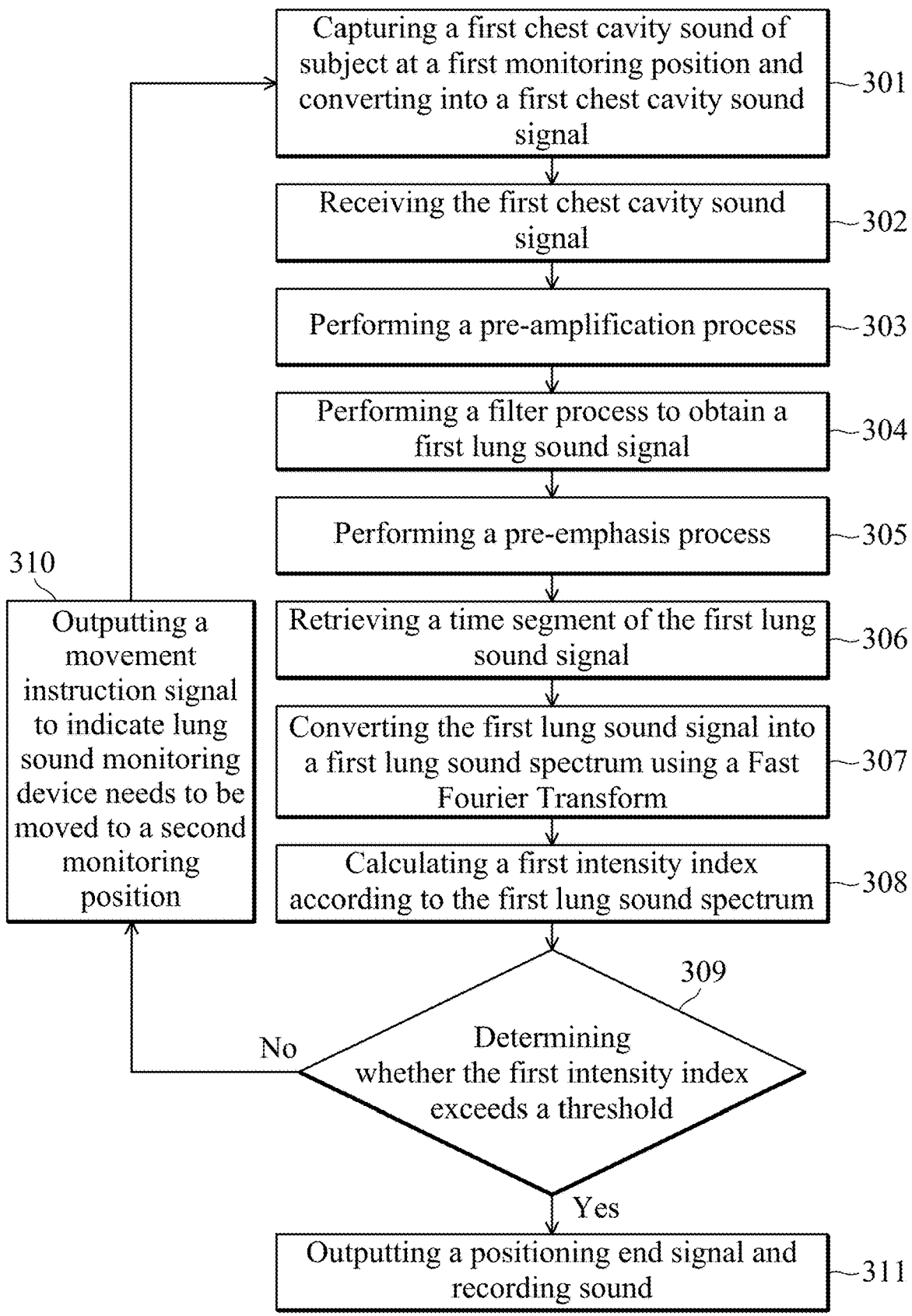
FIG. 3A is a flowchart of a lung sound monitoring method according to an embodiment of the present disclosure.

Referring to FIG. 3A, FIG. 3A is a flowchart of a lung sound monitoring method according to an embodiment of the present disclosure, and the method is used for a lung sound monitoring device 100. After the processor 202 of the lung sound monitoring device 100 loads the execution program, the processor 202 has a predetermined function and can operate the lung sound monitoring method of the present disclosure. In step 301, the acoustic sensor 201 captures the first chest cavity sound of the subject in the first monitoring position and converts it into a first chest cavity sound signal. The acoustic sensor 201 can convert the first chest cavity sound signal into a digital signal using an analog-to-digital converter, and transmit it to the processor 202. In step 302, the processor 202 receives the first chest cavity sound signal from the acoustic sensor 201. In step 303, since the strength of the chest cavity sound signal captured by the acoustic sensor 201 (e.g., a microphone) is usually weak (usually lower than about 20 mV), a pre-amplification process is performed by the processer 202. In step 304, the processor 202 obtains a first lung sound signal that substantially reflects the lung sound of the subject. In one embodiment, the processor 202 performs a band-pass filter process or drives a filter to obtain a signal in a primary lung sound frequency band (e.g., 100-1000 Hz) and to filter out interference from the subject's heart sounds and ambient sounds.

Figure 3B:
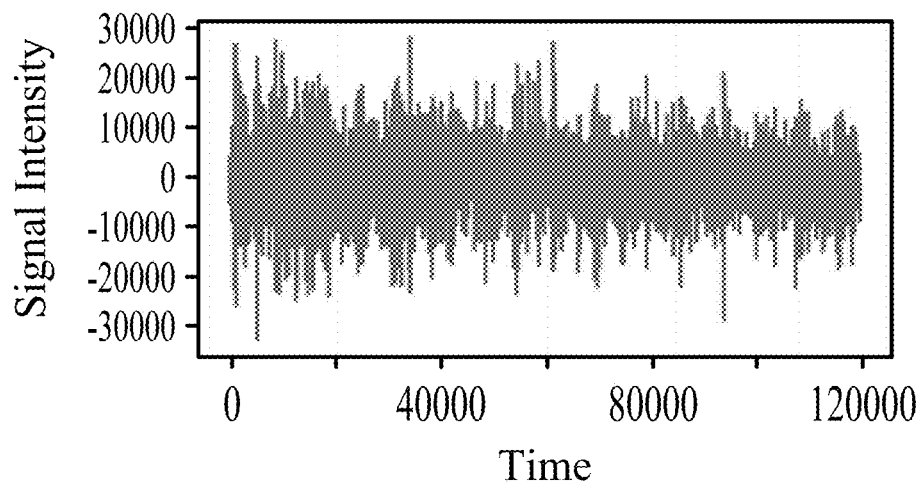
FIG. 3B and FIG. 3C are schematic diagrams before and after the pre-emphasis process according to an embodiment of the present disclosure.
Figure 3C:
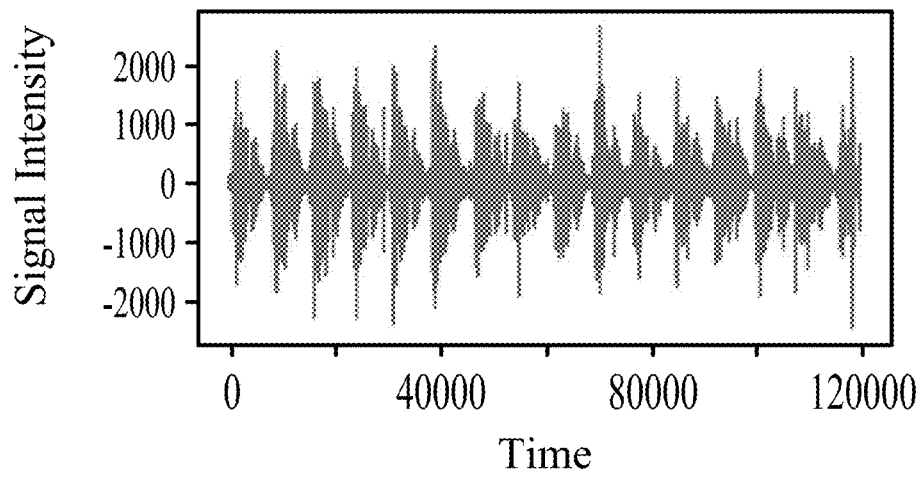

Next, in step 305, the processor 202 performs a pre-emphasis process. The pre-emphasis process operates based on the equation (1) below, so as to compensate for a signal that has been damaged during the filtering out of ambient sounds to obtain a better signal-to-noise ratio. Here, equation (1) is an example and is not limited to such pre-emphasis process.

$$Y_i = X_i - \alpha \times X_{i-1} \quad (1)$$

Wherein Yi is the output signal intensity; i is the time point; α is the pre-emphasis factor; $X_i$ is the signal intensity at the current time, and $X_{i-1}$ is the signal intensity of the previous time point. Referring to FIG. 3B and FIG. 3C, FIG. 3B and FIG. 3C are schematic diagrams before and after the pre-emphasis process according to an embodiment of the present disclosure. In FIG. 3B and FIG. 3C, the intensity units on the vertical axis are the digitized results, and 0 is the normalized intensity on the relative basis. FIG. 3B shows the first lung sound signal before the pre-emphasis process, and FIG. 3C shows the first lung sound signal after the pre-emphasis process. In FIG. 3B and FIG. 3C, the horizontal axis represents time (unit: 1/4000 second), and the vertical axis represents the signal intensity.

In step 306, the processor 202 retrieves a time segment of the first lung sound signal to speed up subsequent data processing and analysis. Wherein, the time segment has a time length and may be set to at least one respiratory cycle (e.g., 3-5 seconds) of the subject. In step 307, the processor 202 converts the first lung sound signal into the first lung sound spectrum using time-domain frequency-domain conversion, wherein the processor 202 may convert the first lung sound signal into the first lung sound spectrum using a Fast Fourier Transform (FFT), and the present disclosure is not limited thereto. It should be noted that the method flow of the embodiment of the present disclosure is exemplary, and the above steps 303 to 306 are not used to limit the implementation order. A person skilled in the art of the present disclosure may adjust the above steps according to actual need.

In step 308, the processor 202 calculates a first intensity index according to the first lung sound spectrum. In the present embodiment, the first intensity index is calculated by the following equation (2).

$$\text{Intensity index} = \frac{\int_a^b \text{amplitude}(x)dx}{\int_0^n \text{amplitude}(x)dx} \quad (2)$$

Wherein a is the lower limit of a preset lung sound frequency band, b is the upper limit of the preset lung sound frequency band, n is the upper limit of the first lung sound spectrum, x is the frequency of lung sound signal, and amplitude (x) is the intensity of the first lung sound spectrum. That is, the intensity index is a ratio obtained by dividing the integral of the intensity of the preset lung sound frequency band by the integral of the intensity of the total lung sound spectrum in the frequency domain. Furthermore, based on clinical experience, it is known that the suitable preset range of the lung sound frequency band is 150 to 750 Hz, and the use of this range for the lung sound frequency band can obtain more representative lung sound information. Therefore, the values of a and b are 150 and 750 Hz, respectively. The n value is the upper limit of the first lung sound spectrum, i.e., the processor 202 obtains the upper limit of the frequency of the main lung sound region after performing the filter process. Generally, the n value is 1000 Hz.

Next, in step 309, the processor 202 outputs a prompt signal according to the first intensity index to indicate whether the first monitoring position is a qualified monitoring position. Specifically, the processor 202 determines whether the first intensity index exceeds a threshold and outputs a prompt signal. The above threshold may be set to 0.75, but the present disclosure is not limited thereto. When the processor 202 determines that the first intensity index does not exceed (i.e., is less than or equal to) the threshold, the first monitoring position is determined to be a non-qualified monitoring position. In step 310, the output prompt signal is a movement instruction signal to indicate that the lung sound monitoring device 100 needs to be moved to a second monitoring position on the subject. For example, the above movement instruction signal may cooperate with the signal of the prompt output device 203 and be displayed as a red light. The lung sound monitoring device 100 may be moved by the subject himself or other medical care assistant. Furthermore, since the lung sound signal is monitored between the ribs of the subject's chest, the movement may be a small distance, for example, 5 mm, but the present disclosure is not limited thereto. In addition, the lung sound monitoring device 100 may set a predetermined time for the subject or medical care assistant to move to a new position. When the predetermined time is over, the lung sound monitoring device 100 automatically determines that it has been moved to the second monitoring position. After moving to the second monitoring position, the lung sound monitoring device 100 returns to step 301 and repeats step 302 to step 309 to recalculate the new intensity index and determine whether new intensity index exceeds the threshold.

Returning to step 309, when the processor 202 determines that the new intensity index exceeds the threshold, the current monitoring position is determined to be a qualified monitoring position. In step 311, the output prompt signal is a positioning-completion signal. The lung sound monitoring device 100 records the lung sound of the subject using the acoustic sensor 201. For example, the positioning-completion signal may be matched with the signal of the prompt output device 203 and displayed as a green light. Furthermore, the data recorded by the lung sound monitoring device 100 can be transmitted to the storage device or server at the back end using the transmission device 204 for subsequent recording, monitoring or analysis. In other embodiments, the lung sound monitoring device 100 may also include a plurality of acoustic sensors 201. Each acoustic sensor 201 is respectively located at different monitoring positions and receives lung sounds obtained from different monitoring positions at the same time. The lung sound waveforms at different positions at the same time are analyzed systematically.

Figure 3D:
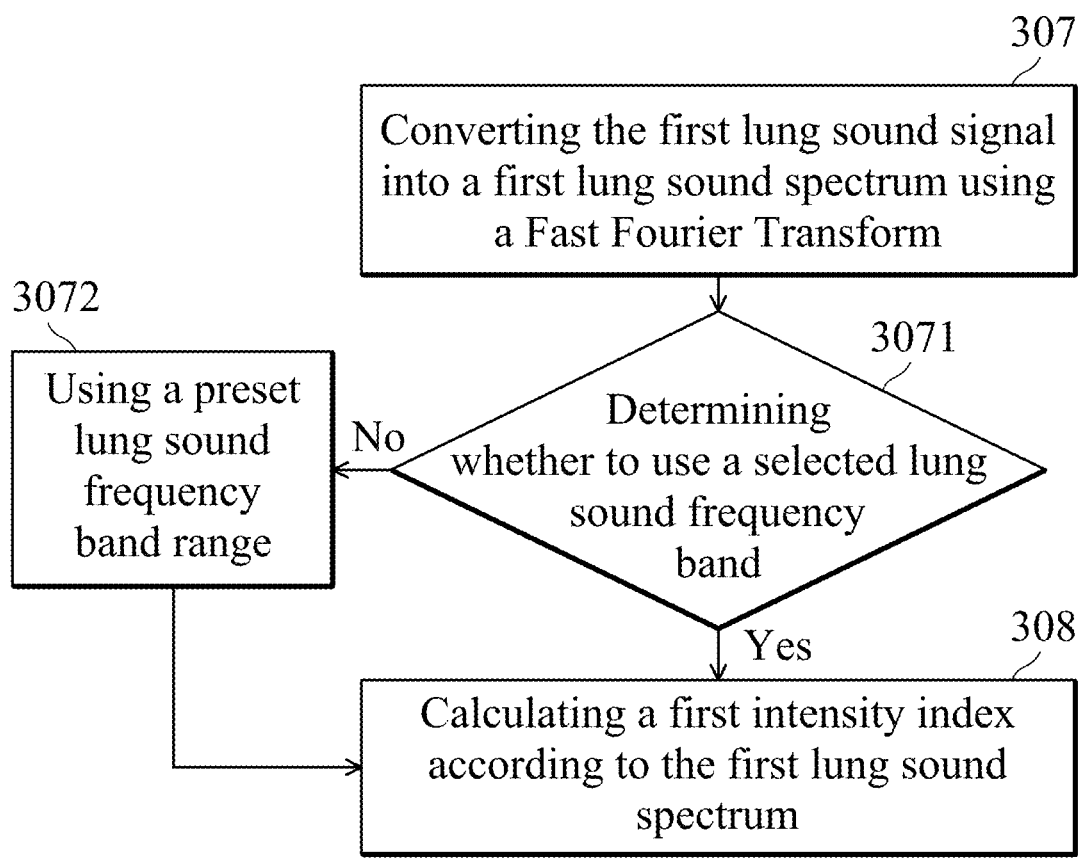
FIG. 3D is another embodiment of the lung sound monitoring method shown in FIG. 3A.

Referring to FIG. 3D, FIG. 3D is another embodiment of the lung sound monitoring method shown in FIG. 3A, which is used for the lung sound monitoring device 100. In this embodiment, after the lung sound monitoring method proceeds to step 307, the method further includes step 3071. In step 3071, before calculating the first intensity index, processor 202 determines whether to use a selected lung sound frequency band. If used, in step 308, the lower and upper limits of the selected lung sound frequency band are set as the a value and the b value in the first intensity index calculation equation. If not used, the method proceeds to step 3072, using a preset lung sound frequency band range (e.g., 150 to 750 Hz), and setting the preset lower limit and upper limit as the a value and the b value in the first intensity index calculation equation. It should be understood that whether or not to select another lung sound frequency band of interest can be set in the lung sound monitoring device 100 through the user interface under the judgment of a medical professional.

Figure 4A:
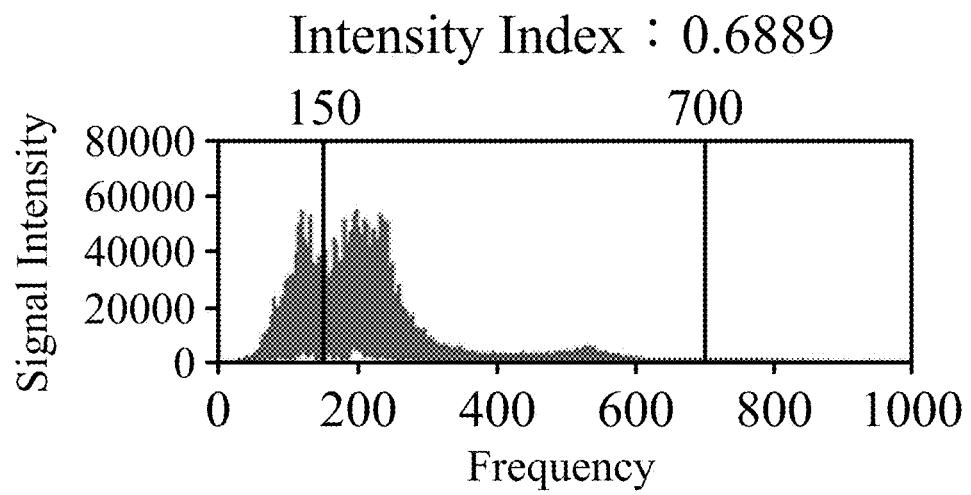
FIG. 4A and FIG. 4B are schematic diagrams of a lung sound spectrum according to an embodiment of the present disclosure.
Figure 4B:
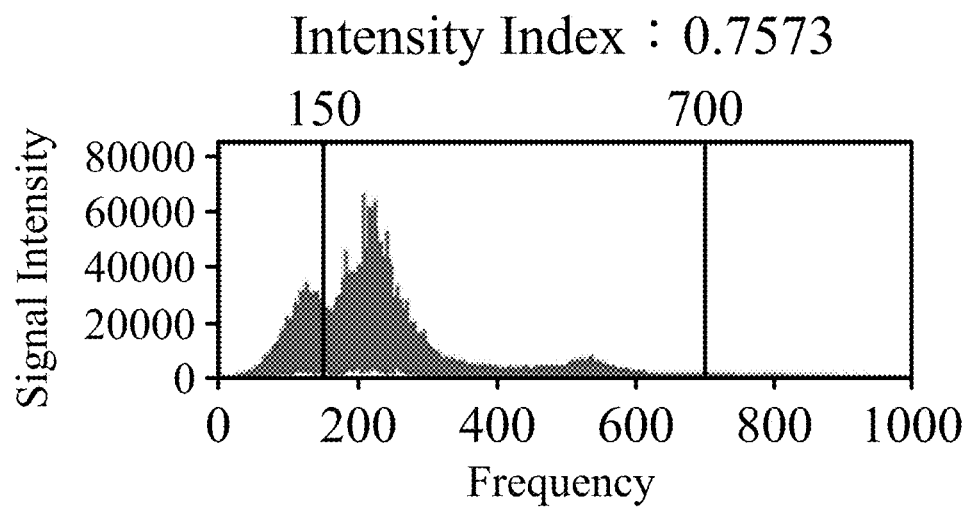

Please refer to FIG. 4A and FIG. 4B. FIG. 4A and FIG. 4B are schematic diagrams of a lung sound spectrum according to an embodiment of the present disclosure. FIG. 4A and FIG. 4B show the lung sound spectrums obtained from the lung sound signals captured at different positions using the Fast Fourier Transform. FIG. 4A shows the first lung sound spectrum obtained at the first monitoring position, and the intensity index calculated by the equation (2) is 0.6889. The processor 202 determines that the intensity index does not exceed the threshold (the threshold is assumed to be 0.75), and the lung sound monitoring device 100 needs to be moved to the second monitoring position after the movement instruction signal is output. FIG. 4B shows the second lung sound spectrum obtained after moving to the second monitoring position. After the calculation, the intensity index is 0.7573. The processor 202 determines that the intensity index exceeds the threshold and sends the positioning-completion signal. The lung sound monitoring device 100 starts to record the lung sound of the subject. In addition, in the present embodiment, the selected lung sound frequency band is not used, but the analysis is performed using the preset lung sound frequency band. Therefore, the mark lines on the left side and the right side in FIG. 4A and FIG. 4B are 150 and 700 hertz, respectively. In FIG. 4A and FIG. 4B, the horizontal axis represents the frequency (unit: Hertz), and the vertical axis represents the signal intensity.

Figure 5:
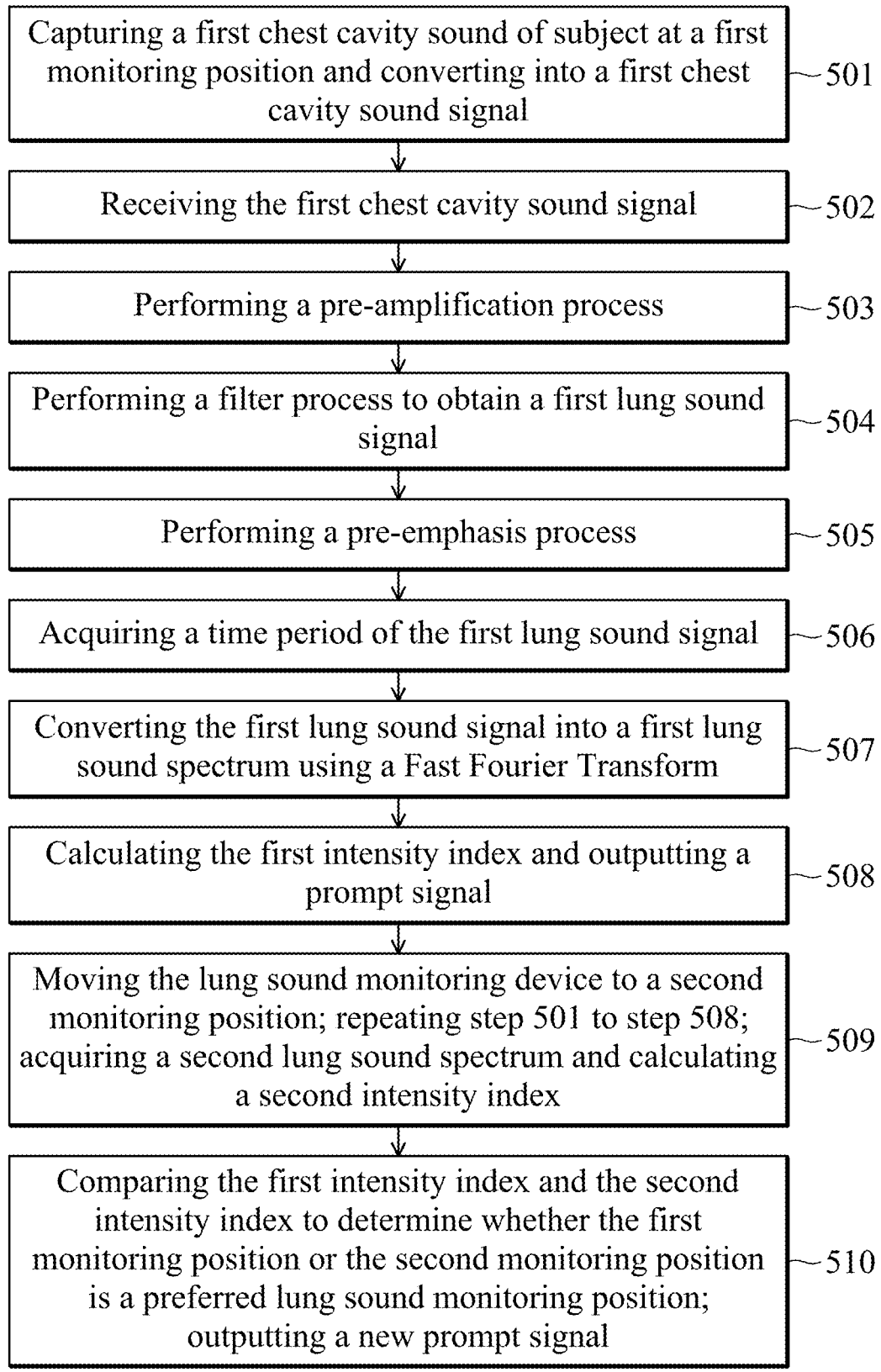
FIG. 5 is a flowchart of a lung sound monitoring method according to another embodiment of the present disclosure.

FIG. 5 is a flowchart of a lung sound monitoring method according to another embodiment of the present disclosure, which is used for a lung sound monitoring device 100. The same steps in the flowchart of the lung sound monitoring method shown in FIG. 5 and FIG. 3A are also performed as described above, and will not be described here. The main differences between FIG. 5 and FIG. 3A are that in step 508, after the processor 202 calculates the first intensity index, it outputs a prompt signal to indicate whether the first monitoring position is a qualified monitoring position. Wherein, the first intensity index can be calculated and obtained according to equation (2). In addition, the processor 202 may output the corresponding prompt signal according to whether the first intensity index exceeds the threshold. In one embodiment, when the first intensity index does not exceed the threshold, the prompt signal is a movement instruction signal. The processor 202 outputs the movement instruction signal to indicate that the lung sound monitoring device 100 needs to be moved to a second monitoring position on the subject.

After the processor 202 outputs the prompt signal, proceeding to step 509, the lung sound monitoring device 100 is moved to a second monitoring position on the subject. The acoustic sensor 201 captures the chest cavity sound of the subject at the second monitoring position and converts into a second chest cavity sound signal. Then, the processor 202 receives the second chest sound signal and performs the filter process to obtain a second lung sound signal that substantially reflects the lung sound of the subject. The processor 202 converts the second lung sound signal into the second lung sound spectrum using time-domain frequency-domain conversion. The processor 202 calculates a second intensity index based on the second lung sound spectrum. In brief, step 501 to step 508 are repeated to calculate the second intensity index.

In step 510, the processor 202 further compares the first intensity index and the second intensity index to determine whether the first monitoring position or the second monitoring position is a suitable lung sound monitoring position. Furthermore, the processor 202 may determine the first monitoring position or the second monitoring position as the suitable lung sound monitoring position according to the difference between the first intensity index and the second intensity index, and update and output a new prompt signal. The prompt output device 203 may output a corresponding prompt signal after comparing the first intensity index and the second intensity index. For example, the lung sound monitoring device 100 may indicate the corresponding prompt signal by the change of light signal or the level of vibration of the prompt output device 203, or by displaying the intensity in a long strip through the plurality of light signals. Through the above steps, the lung sound monitoring device 100 may indicate the subject or medical care assistant whether the current monitoring position is a suitable lung sound monitoring position and may help to determine a better lung sound receiving position. Furthermore, the subject or medical care assistant may decide whether to continue moving the monitoring position to obtain a better lung sound monitoring position, and finally perform subsequent recording, monitoring or analysis.

Figure 6:
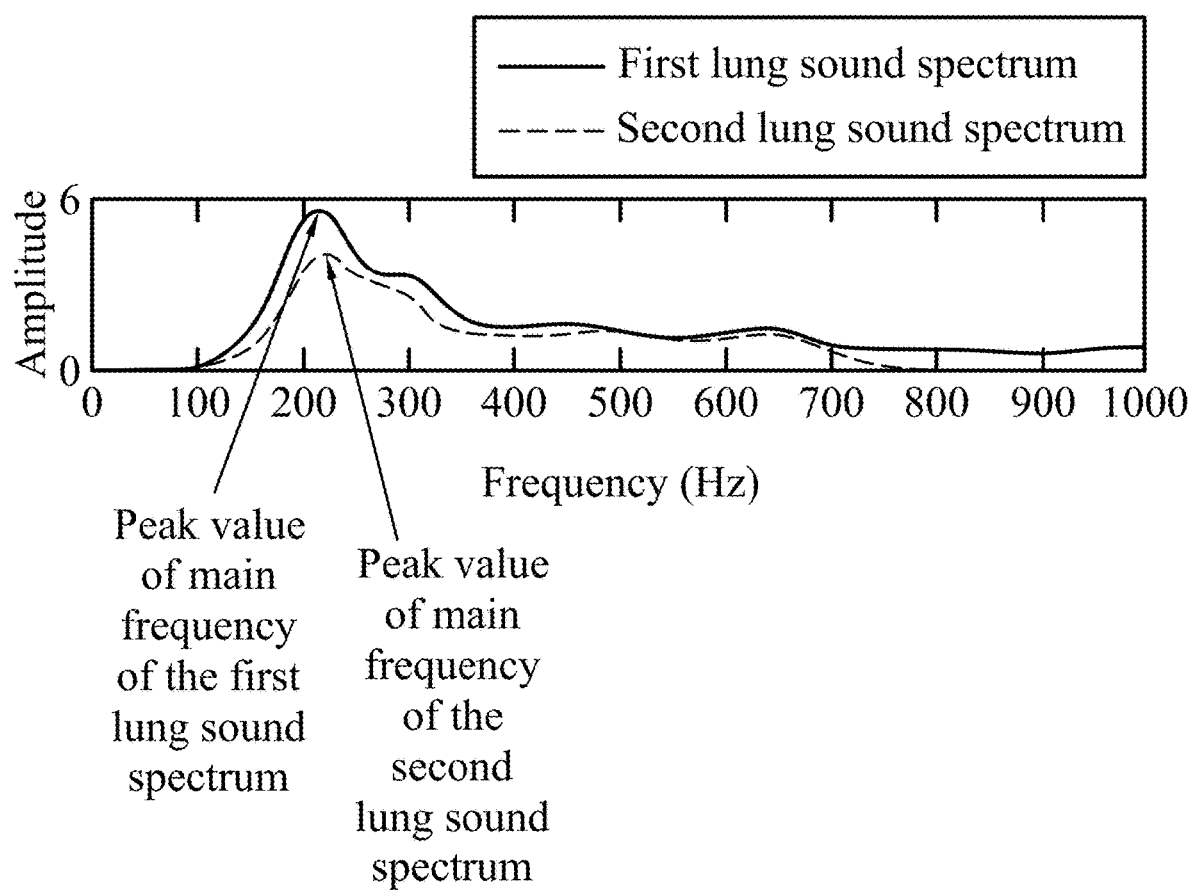
FIG. 6 is a schematic diagram of a calculation intensity index according to another embodiment of the present disclosure.

In another embodiment of the present disclosure, the above-mentioned first intensity index and second intensity index can be calculated in a different way. Please refer to FIG. 6. FIG. 6 is a schematic diagram of a calculation intensity index according to another embodiment of the present disclosure. In detail, the first intensity index and the second intensity index derived by the processor 202 are peak values of the main frequency obtained in the first lung sound spectrum and the second lung sound spectrum, respectively. As shown in FIG. 6, the peak value of the main frequency of the first lung sound spectrum obtained from the first monitoring position is greater than the peak value of the main frequency of the second lung sound spectrum obtained from the second monitoring position. Therefore, the processor 202 determines that the first monitoring position is a better monitoring position than the second monitoring position and outputs a corresponding prompt signal. In FIG. 6, the horizontal axis represents the frequency (unit: Hertz), the vertical axis represents the amplitude of the measured signal, and the vertical axis may also represent the energy or intensity of the signal, but the present disclosure is not limited thereto.

The lung sound monitoring device and the lung sound monitoring method provided by the present disclosure may improve upon the current state of diagnosis of pulmonary obstruction patients, who need to be auscultated by an experienced clinician personally holding a stethoscope, and according to personal experience to achieve a good monitoring position. The lung sound monitoring device and the lung sound monitoring method provided by the present disclosure may help the subject or medical care assistant to judge whether the lung sound monitoring device is in a better lung sound receiving position. Furthermore, it provides a function of continuous lung sound recording for subsequent monitoring and analysis of the patient's condition.

Data transmission methods, or certain aspects or portions thereof, may take the form of program code (i.e., executable instructions) embodied in tangible media, such as floppy diskettes, CD-ROMS, hard drives, or any other machine-readable storage medium, wherein, when the program code is loaded into and executed by a machine such as a computer, the machine thereby becomes an apparatus for practicing the methods. The methods may also be embodied in the form of program code transmitted over some transmission medium, such as electrical wiring or cabling, through fiber optics, or via any other form of transmission, wherein, when the program code is received and loaded into and executed by a machine such as a computer, the machine becomes an apparatus for practicing the disclosed methods. When implemented on a general-purpose processor, the program code combines with the processor to provide a unique apparatus that operates analogously to application-specific logic circuits.

While the disclosure has been described by way of example and in terms of the suitable embodiments, it is to be understood that the disclosure is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A lung sound monitoring device, comprising:
an acoustic sensor, for capturing a chest cavity sound of a subject at a first monitoring position on the subject and converting the chest cavity sound into a first chest cavity sound signal; and
a processor, for receiving the first chest cavity sound signal and performing a filter process to obtain a first lung sound signal, and converting the first lung sound signal into a first lung sound spectrum using time-domain frequency-domain conversion; wherein
the processor acquires a first intensity index according to the first lung sound spectrum, and outputs a prompt signal according to the first intensity index to indicate whether the first monitoring position is a qualified monitoring position;
wherein the first intensity index is calculated by an equation, as indicated below:

$$\text{Intensity index} = \frac{\int_a^b \text{amplitude}(x)dx}{\int_0^n \text{amplitude}(x)dx},$$

wherein a is lower limit of a preset lung sound frequency band; b is upper limit of the preset lung sound frequency band; n is upper limit of the first lung sound spectrum; x is a frequency of the first lung sound signal; amplitude(x) is the intensity of the first lung sound spectrum.

2. The lung sound monitoring device as claimed in claim 1, wherein the processor generates the prompt signal according to whether the first intensity index exceeds a threshold; when the first intensity index does not exceed the threshold, the prompt signal is a movement instruction signal to indicate that the lung sound monitoring device needs to be moved to a second monitoring position on the subject; when the first intensity index exceeds the threshold, the prompt signal is a positioning-completion signal, and the lung sound monitoring device starts to record the lung sound of the subject.

3. The lung sound monitoring device as claimed in claim 2, wherein after outputting the movement instruction signal and moving the lung sound monitoring device to the second monitoring position on the subject, the acoustic sensor captures the chest cavity sound of the subject at the second monitoring position and converts the chest cavity sound into a second chest cavity sound signal;
the processor receives the second chest cavity sound signal and performs the filter process to obtain a second lung sound signal, and converts the second lung sound signal into a second lung sound spectrum using time-domain frequency-domain conversion; the processor acquires a second intensity index according to the second lung sound spectrum;
the processor further compares the first intensity index and the second intensity index to determine whether the first monitoring position or the second monitoring position is a suitable lung sound monitoring position.

4. The lung sound monitoring device as claimed in claim 1, wherein the processor further performs a pre-amplification process and a pre-emphasis process after receiving the first chest cavity sound signal.

5. The lung sound monitoring device as claimed in claim 1, wherein before converting the first lung sound signal using time-domain frequency-domain conversion, the processor retrieves a time segment of the first lung sound signal, and the time segment has a time length at least equal to one respiratory cycle of the subject.

6. The lung sound monitoring device as claimed in claim 1, wherein before calculating the first intensity index, the processor further determines whether to use a selected lung sound frequency band, and when the selected lung sound frequency band is used, setting lower limit and upper limit of the selected lung sound frequency band as values of a and b in the equation of the first intensity index.

7. The lung sound monitoring device as claimed in claim 3, wherein the first intensity index is derived from a peak value of main frequency in the first lung sound spectrum, and the second intensity index is derived from the peak value of the main frequency in the second lung sound spectrum.

8. The lung sound monitoring device as claimed in claim 1, further comprising a prompt output device, configured to output the prompt signal, wherein the prompt signal is presented as vibration, sound, light signal or a combination thereof.

9. The lung sound monitoring device as claimed in claim 1, further comprising a transmission device, configured to transmit the first chest cavity sound signal, the first lung sound signal or the first intensity index to a storage device or a cloud server for subsequent recording, monitoring or analysis.

10. A lung sound monitoring method for a lung sound monitoring device which comprises an acoustic sensor and a processor, the method comprising:
capturing a chest cavity sound of a subject at a first monitoring position on the subject by the acoustic sensor and converting the chest cavity sound into a first chest cavity sound signal;

receiving the first chest cavity sound signal using the processor and performing a filter process to obtain a first lung sound signal, and converting the first lung sound signal into a first lung sound spectrum using time-domain frequency-domain conversion;

acquiring a first intensity index by the processor according to the first lung sound spectrum, and outputting a prompt signal according to the first intensity index to indicate whether the first monitoring position is a qualified monitoring position;

wherein the first intensity index is calculated by the equation below:

$$\text{Intensity index} = \frac{\int_a^b \text{amplitude}(x)dx}{\int_0^n \text{amplitude}(x)dx},$$

wherein a is the lower limit of the preset lung sound frequency band; b is the upper limit of the preset lung sound frequency band; n is the upper limit of the first lung sound spectrum; x is the frequency of the first lung sound signal; amplitude(x) is the intensity of the first lung sound spectrum.

11. The lung sound monitoring method as claimed in claim 10, wherein the processor generates the prompt signal according to whether the first intensity index exceeds a threshold; when the first intensity index does not exceed the threshold, the prompt signal is a movement instruction signal to indicate that the lung sound monitoring device needs to be moved to a second monitoring position on the subject; when the first intensity index exceeds the threshold, the prompt signal is a positioning-completion signal, and the lung sound monitoring device starts to record the lung sound of the subject.

12. The lung sound monitoring method as claimed in claim 11, wherein after outputting the movement instruction signal and moving the lung sound monitoring device to the second monitoring position on the subject, the acoustic sensor captures the chest cavity sound of the subject at the second monitoring position and converts the chest cavity sound into a second chest cavity sound signal;

the processor receives the second chest cavity sound signal and performs the filter process to obtain a second lung sound signal, and converts the second lung sound signal into a second lung sound spectrum using time-domain frequency-domain conversion; the processor acquires a second intensity index according to the second lung sound spectrum;

the processor further compares the first intensity index and the second intensity index to determine whether the first monitoring position or the second monitoring position is a suitable lung sound monitoring position.

13. The lung sound monitoring method as claimed in claim 10, further comprising using the processor to perform a pre-amplification process and a pre-emphasis process after receiving the first chest cavity sound signal.

14. The lung sound monitoring method as claimed in claim 10, wherein before converting the first lung sound signal using time-domain frequency-domain conversion, the processor retrieves a time segment of the first lung sound signal, and the time segment has a time length at least equal to one respiratory cycle of the subject.

15. The lung sound monitoring method as claimed in claim 10, wherein before calculating the first intensity index, the processor further determines whether to use a selected lung sound frequency band, and when the selected lung sound frequency band is used, setting the lower limit and the upper limit of the selected lung sound frequency band as values of a and b in the equation of the first intensity index.

16. The lung sound monitoring method as claimed in claim 12, wherein the first intensity index is derived from a peak value of main frequency in the first lung sound spectrum, and the second intensity index is derived from the peak value of the main frequency in the second lung sound spectrum.

17. The lung sound monitoring method as claimed in claim 10, wherein the lung sound monitoring device further comprises a prompt output device, and the method further comprises outputting the prompt signal by the prompt output device, wherein the prompt signal is presented as a vibration, a sound, a light signal, or a combination thereof.

18. The lung sound monitoring method as claimed in claim 10, wherein the lung sound monitoring device further comprises a transmission device, and the method further comprises transmitting the first chest cavity sound signal, the first lung sound signal or the first intensity index via the transmission device to a storage device or a cloud server for subsequent recording, monitoring or analysis.

* * * * *